United States Patent [19]

Nowak et al.

[11] Patent Number: 4,834,731
[45] Date of Patent: May 30, 1989

[54] OSTOMY APPLIANCE AND CONVEX PRESSURE RING ASSEMBLY THEREFOR

[75] Inventors: George M. Nowak, Lake Villa; Wagdi W. Habib, Barrington, both of Ill.

[73] Assignee: Hollister Incorporated, Libertyville, Ill.

[21] Appl. No.: 122,836

[22] Filed: Nov. 19, 1987

[51] Int. Cl.⁴ .............................................. A61F 5/44
[52] U.S. Cl. .................................................. 604/339
[58] Field of Search ............................. 604/332–345, 604/277

[56] References Cited

U.S. PATENT DOCUMENTS

| | | | |
|---|---|---|---|
| D. 257,063 | 9/1980 | Galindo | D24/4 |
| 3,283,757 | 11/1966 | Nelson | 604/342 |
| 4,213,458 | 7/1980 | Nolan et al. | 128/283 |
| 4,219,023 | 8/1980 | Galindo | 604/344 |
| 4,477,325 | 10/1984 | Osburn | 204/159.12 |
| 4,496,357 | 1/1985 | Osburn | 604/336 |
| 4,592,750 | 6/1986 | Kay | 604/337 |
| 4,650,817 | 3/1987 | Allan, Jr. et al. | 604/344 |
| 4,710,182 | 12/1987 | Bryson | 604/339 |
| 4,723,952 | 2/1988 | Esposito | 604/338 |

OTHER PUBLICATIONS

Product Flyer entitled "Marlen's New Ultra," Marlen Mfg. & Dev. Co. 1987.

Primary Examiner—C. Fred Rosenbaum
Assistant Examiner—J. Kruter
Attorney, Agent, or Firm—Tilton, Fallon, Lungmus

[57] ABSTRACT

A convex pressure ring assembly, and its combination with an ostomy appliance, for exerting peristomal pressure to cause protrusion of a stoma into the openings of a faceplate and pouch and thereby promote more effective operation of the collection appliance. The pressure ring assembly is applied to the proximal (patient-facing) surface of the faceplate and includes a distal support ring of convex configuration formed of relatively rigid plastic, an intermediate ring of resilient, thermoformable material, and a proximal ring of soft, deformable, moisture-absorbing skin barrier material having both dry and wet tack.

25 Claims, 4 Drawing Sheets

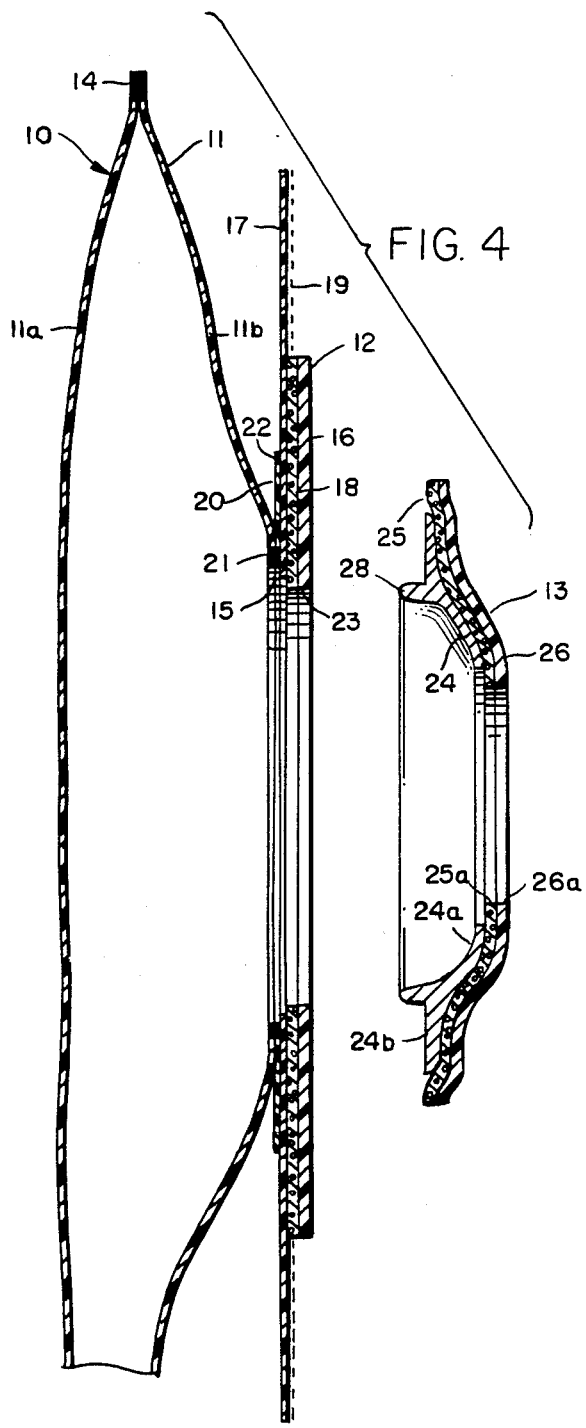
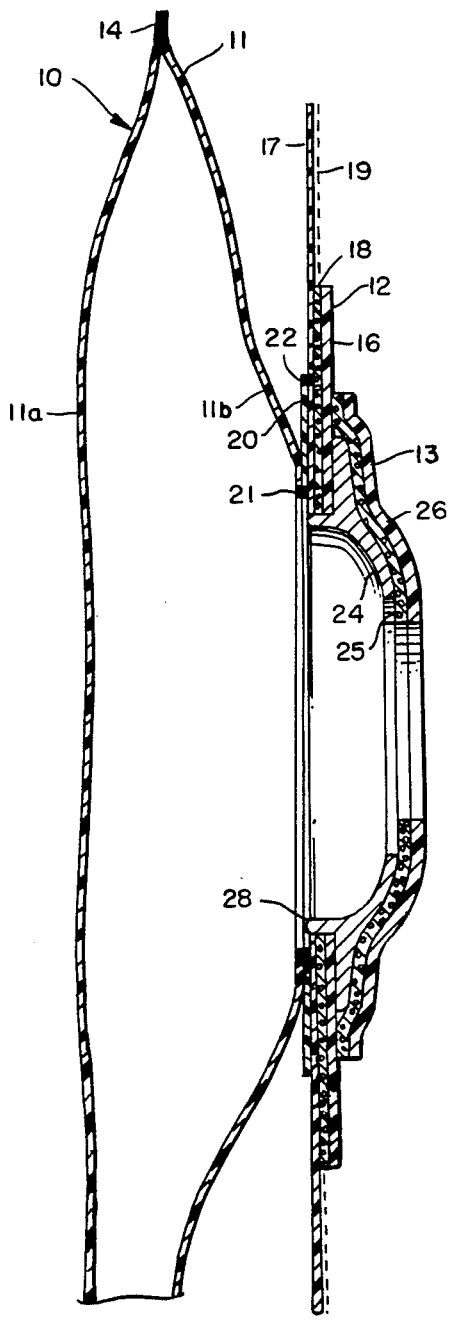
FIG. 4
FIG. 5

OSTOMY APPLIANCE AND CONVEX PRESSURE RING ASSEMBLY THEREFOR

BACKGROUND

Ostomy patients with flush or recessed stomas have found that if external pressure is applied in the peristomal region, sufficient protrusion of the stoma may occur to aid in the discharge of effluent directly into the collection pouch, thereby prolonging the effectiveness of the adhesive seal between the faceplate and the peristomal skin surfaces. Skin irritation and patient discomfort may also be greatly reduced. In some cases, such pressure has been applied by means of a sealing ring formed of karaya or other soft, pliable, skin barrier material; however, the deformability and cold-flowability of such a ring limits its effectiveness, or at least the duration of its effectiveness, in achieving adequate stomal protrusion. Some manufacturers of ostomy appliances have therefore introduced relatively rigid convex annular inserts for use with the coupling rings of adhesive faceplates having skin barrier wafers attached thereto. In theory, such an insert is intended to deform the skin barrier wafer to increase peristomal pressure when the appliance is worn but, in practice, the insert usually lacks sufficient convexity to produce a significant change in the contour of the wafer. Inserts with greater convexity have been unavailable, presumably because of the excessive forces that would seem to be necessary, and the damage a faceplate coupling ring might sustain, in fitting such an insert into place. A conventional convex insert has the further disadvantage of requiring attachment from the outer or distal side of a faceplate. Consequently, in the case of a two-piece appliance with disconnectable coupling rings, there is the risk, indicated above, that the faceplate coupling ring might be deformed or damaged when the insert is forced into place; in the case of a one-piece appliance, where a pouch and faceplate are permanently connected, there is the inconvenience that the insert must be fed upwardly through the drainage opening of the pouch so that it may be snapped into position from within the pouch.

SUMMARY

Unlike a conventional convex insert, the convex pressure ring assembly of this invention is not secured to a faceplate from its distal side (the side facing away from the patient) but is instead attached to its proximal side, thereby overcoming major problems associated with the use of prior devices. The convex pressure ring assembly of this invention may be secured to the proximal face of such a faceplate either by the user or the manufacturer. Of particular importance is the fact that the external application of such a pressure ring assembly to the proximal surface of a faceplate allows the pressure ring to be contoured with more pronounced convexity, thereby producing greater stomal protrusion, without the dimensional and configurational constraints encountered in the design of earlier constructions requiring attachment from the distal side of a faceplate.

An important aspect of this invention lies in the discovery that a particularly effective convex pressure ring assembly is achieved when three elements are combined together for attachment to the proximal surface of a faceplate. One component takes the form of a relatively rigid support ring, preferably formed of thermoplastic material, having integral inner and outer wall portions. The inner wall portion has a central opening and is convexly curved in a proximal direction. The second component comprises an intermediate ring of soft, resilient, moisture-impermeable, thermoformable material which is secured to the convex proximal surface of the rigid support ring. The third component is a barrier ring of soft, deformable, moisture-absorbing skin barrier material having both dry and wet tack. The barrier ring extends over the proximal surface of the intermediate ring, and both the intermediate ring and the barrier ring have border portions that extend radially outwardly beyond the periphery of the plastic support ring. In addition, the intermediate and barrier rings may have pre-formed openings aligned with, but substantially smaller than, the opening of the rigid support ring. In use of the assembly, contact with a patient's stoma, if it occurs at all, tends to be made only by the soft intermediate and the skin barrier layers, since those layers or rings have openings of smaller inside diameter than the rigid support ring. The outer border portions of the intermediate and barrier rings are sealingly secured to the proximal surface of an adhesive faceplate which, in a preferred embodiment of the invention, may be lined with a layer of similar barrier material also having surface tack. Therefore, the annular border portion of the intermediate ring projecting beyond the periphery of the rigid support ring is sandwiched between, and sealed to, the barrier ring of the convex pressure ring assembly and the adhesive surface of the faceplate or, if the faceplate is provided with a skin barrier layer, then the adhesive surface of the barrier layer or liner of that faceplate.

The intermediate ring is preferably formed of a soft, compressible, thermoplastic foam and forms a cushion between the skin barrier ring and the rigid support ring of the pressure ring assembly. In addition, such a foam ring is highly effective in controlling or limiting the extent of cold flow of the skin barrier ring. In effect, the foam serves as a resilient and elastic backing having surface openings and irregularities into which the barrier material flows and becomes interlocked. Forces tending to displace the material of the skin barrier ring outwardly or inwardly are restrained by the resilient foam. If such forces are great enough to cause inward or outward deformation of both the barrier ring and its elastic foam backing then, upon reduction of such forces, the recovery action of the foam also tends to cause some recovery of the barrier ring's original shape. Therefore, while cold flow of the barrier material is still possible, such flow is substantially limited, at least in certain directions, by the foam intermediate ring.

In the case of a two-piece appliance, the coupling ring of the faceplate may be an integral extension of the relatively rigid support ring, thereby providing an appliance of reduced profile. Such profile may be further reduced by locating the latching sealing means for the two rings within the concavity of the faceplate ring.

Other advantages, features, and objects of the invention will become apparent from the specification and drawings.

DRAWINGS

FIG. 4 is a vertical cross sectional view illustrating a faceplate-equipped pouch and a convex pressure ring assembly with the two subassemblies in separated condition.

FIG. 5 is a vertical sectional view similar to FIG. 4 but illustrating the subassemblies in joined condition.

DETAILED DESCRIPTION OF PREFERRED EMBODIMENTS

Figure 1:
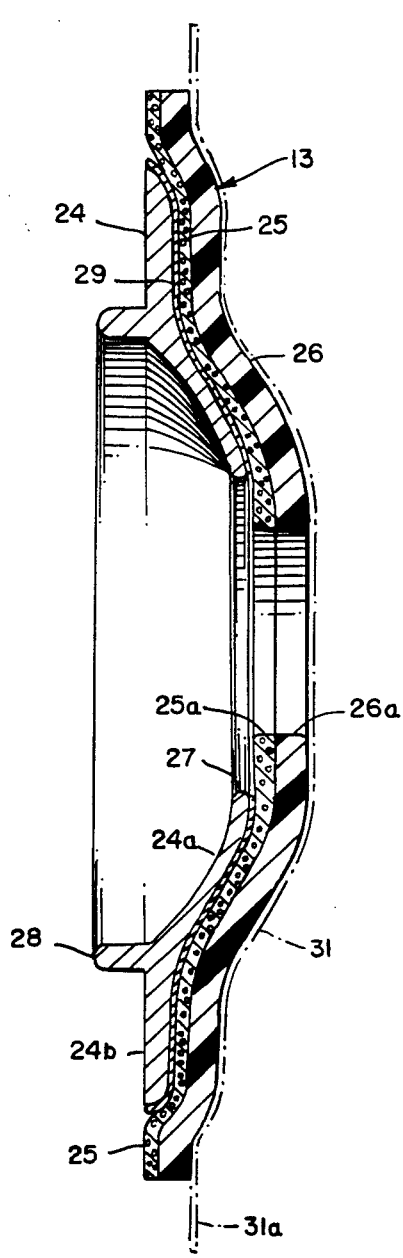
FIG. 1 is an enlarged cross sectional view of a convex pressure ring assembly embodying the present invention.

Referring to the drawings, the numeral 10 generally designates an ostomy appliance composed of a collection pouch 11 and a faceplate 12, the latter being equipped with a convex pressure ring assembly 13 (FIG. 5). As shown most clearly in FIG. 4, the pressure ring assembly 13 is an added feature to an otherwise complete ostomy appliance and is designed to be secured to faceplate 12 either by the manufacturer or the user. Pouch 11 is conventional and includes distal (front) and proximal (rear) walls 11a and 11b sealed together along their peripheral edges by heat seal bond 14. As is well known, the pouch may be formed of any suitable thermoplastic film that is impermeable to liquids such as, for example, low-density polyethylene.

Pouch wall 11b, referred to as a proximal wall or panel because it is in closer proximity to the patient when the appliance is worn, is provided with a stoma-receiving opening 15 near its upper end. The faceplate 12, which is secured to the proximal wall of the pouch about the stoma opening, essentially comprises a microporous patch 17 coated on its proximal surface with an adhesive layer 19 (schematically represented in FIGS. 4 and 5 by a dotted line) formed of any suitable hypoallergenic, medical-grade, pressure-sensitive adhesive that is permeable to gas and water vapor. A typical medical-grade acrylic adhesive has been found effective, but other adhesives having similar properties may be used.

In the preferred embodiment shown, a skin barrier layer or ring 16 is also disposed on the proximal side of the microporous patch 17 and a soft resilient layer or ring 18 of plastic foam is interposed between the skin barrier ring 16 and the microporous patch.

The protective skin barrier ring 16 is formed of a soft, pliable, water-absorbing material having both dry and wet tack. A variety of such compositions are known in the art and may be used. Karaya-glycerin formulations, mixtures of polyacrylamide resin and other polyols, and mixtures of elastomers and hydrocolloids may be used. Reference may be had to U.S. Pat. No. 4,477,325 and 4,496,357 for a discussion of prior skin barrier compositions and a disclosure of additional compositions having advantages which may also be utilized here.

The porous patch 17 is advantageously formed of non-woven microporous sheet material of the type disclosed in U.S. Pat. No. 4,213,458. A non-woven microporous material of polyester fibers is believed particularly suitable. The microporous material should have gas and water vapor transmission characteristics sufficiently high to permit the release of water vapor and gases from the skin at a rate high enough to avoid the retention and accummulation of liquid on the surface of the skin covered by the patch.

The intermediate layer or ring 18 is formed of soft, flexible, and resilient thermoplastic foam that is both liquid and gas impermeable. While any thermoplastic foam having such characteristics may be used, particularly effective results have been obtained using a closed-cell polyethylene foam having a general thickness within the range of about 0.3 to 10 millimeters, preferably 0.5 to 5 millimeters. The foam layer is secured to the microporous patch 12 by adhesive coating 19 and to the skin barrier layer 16 by the adhesive properties of the skin barrier material. It provides a soft, resilient cushion between the skin barrier layer and the microporous patch and restrains cold flow of the skin barrier material. While their inclusion as elements of the faceplate is highly advantageous, either the foam layer 18 or the barrier layer 16, or both, may be omitted in those circumstances where their advantages may be deemed unnecessary. Where only the barrier layer 16 is omitted, a layer of suitable adhesive, such as the adhesive used for coating 19, would be applied to the proximal face of foam ring 18. As indicated both the pliant skin barrier layer 16 and the foam layer 18 may be omitted in some circumstances, leaving as the basic element of the faceplate only the adhesive-coated microporous patch 12. That patch is secured to the wall 11b of the pouch by means of a thermoplastic connecting ring 20. The distal side of the ring 20 is attached to wall 11a along an annular heat seal zone 21 about stoma opening 15, and the periphery of the ring is secured to the patch along heat seal zone 22. Reference may be had to U.S. Pat. No. 4,213,458 for details of the intermediate ring construction and its advantages. It will be observed that the faceplate 12 has a central opening 23 aligned with pouch opening 15 with a size approximately the same as, or only slightly smaller than, the pouch opening.

Figure 2:
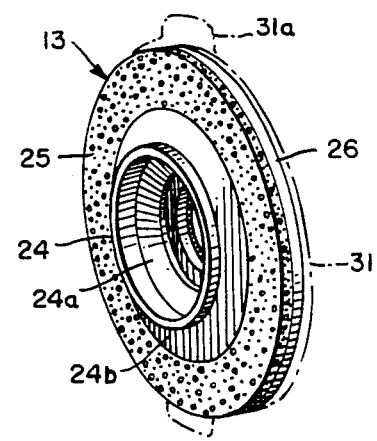
FIG. 2 is a perspective view illustrating the convex pressure ring assembly viewed from its distal side.
Figure 3:
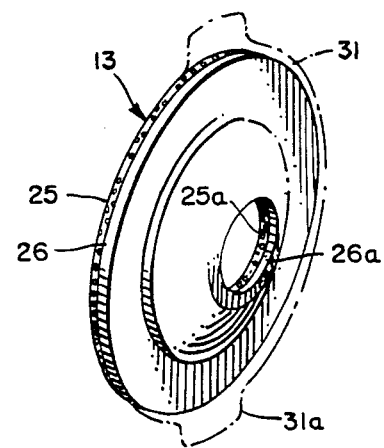
FIG. 3 is a perspective view showing the convex pressure ring assembly viewed from its proximal side.

FIGS. 1–3 illustrate the convex pressure ring assembly in detail. The assembly includes a relatively rigid support ring 24, an intermediate foam ring 25, and a proximal barrier ring 26. The term "relatively rigid" is here used to mean that the support ring 24 retains its distinctive shape under normal conditions of use. While various materials may be used for the support ring, rigid or semi-rigid plastics, such as polypropylene, polyethylene, or polystyrene are considered particularly suitable. The support ring includes integral inner and outer wall portions 24a and 24b, the inner wall portion having a central opening 27 aligned with (or alignable with) the stoma openings of the faceplate and pouch. Although the outer wall portion 24b is generally planar, the inner wall portion 24a curves inwardly and proximally, giving the faceplate a convex curvature in a proximal direction about the central opening 27. An integral annular flange 28 projects distally from the support ring in an area between the ring's inner and outer wall portions. As shown in FIGS. 4 and 5, the diameter of flange 28 is the same or slightly smaller than the inside diameter of faceplate opening 23.

The intermediate foam ring 25 is composed of a soft, resilient, liquid and gas impermeable, thermoformable material. A resilient foam of polyethylene, polyurethane, or other polymeric material having similar properties is believed particularly suitable. In a preferred embodiment, the intermediate ring 25 is formed of the same resilient thermoplastic foam as the foam layer 18 of the faceplate. In general, the thickness of ring 25 should fall within the range of about 0.3 to 10 millimeters, preferably about 0.5 to 5 millimeters. As shown in FIG. 1, the foam ring is secured to the proximal face of support ring 24 by means of a pressure-sensitive adhesive layer 29. Such adhesive may be any medical-grade acrylic adhesive, or other suitable pressure-sensitive or hot melt adhesive, and may be sprayed or otherwise applied to the proximal face of the support ring (or to the distal face of the foam ring) prior to assembly of the parts.

Barrier ring 26, like the skin barrier layer 16 of the faceplate, may be formed from any of a variety of soft, pliable, moisture-absorbing skin barrier materials having both dry and wet tack. A characteristic of such skin barrier materials is the tendency to flow or migrate in response to deforming forces. An important function of the contoured foam ring 25 is that by being in adhesive contact with the barrier ring (by reason of the surface tack of the skin barrier material), it limits such migration or flow of the barrier ring. Because of the recoverability of the foam ring when distorting forces are relieved, the foam ring also tends to restore the shape of the barrier ring when distorting forces are removed or reduced. These advantages are accomplished while at the same time the intermediate foam ring serves as a cushion between the rigid support ring 24 and the skin barrier ring 26. The result is an assembly in which the support ring functions primarily to maintain the convex configuration of the assembly, the skin barrier ring provides a soft, protective, non-irritating sealant layer against the wearer's skin, and the resilient foam ring 25 serves as a cushioning layer that also limits the extent of migration of the skin barrier ring 26.

The foam intermediate ring 25 and the skin barrier ring 26 may be thermoformed together into the convex cross-sectional contour illustrated in the drawings. Both layers may first be laminated together in planar condition and then subjected to heat and pressure (or vacuum) against a suitable mold or form to produce the convex configuration illustrated. Since thermoforming procedures are well known, further discussion of the details of such an operation is believed unnecessary herein.

It will also be observed that the skin barrier ring 26 and intermediate foam ring 25 have aligned openings 26a and 25a, respectively, that are in register with, but substantially smaller than, the opening 27 in support ring 24. Ideally, openings 25a and 26a are pre-formed at the time of manufacture but, if desired, they may be formed or cut by the user at the time of application of the device. In addition, the skin barrier ring 26 may have a substantially larger outside diameter than support ring 24. Specifically, the skin barrier ring may have an outer border portion 26b that projects radially outwardly beyond the periphery of support ring 24. In the embodiment illustrated, the foam ring is coextensive with the barrier ring 26 and, therefore, has an outer border portion 25b that also projects outwardly beyond the periphery of the support ring. It is important that at least the barrier ring be provided with such an outwardly projecting border portion so that sealing engagement may occur between the pliable proximal layer or layers of the pressure ring assembly and the faceplate 12. Manufacturing procedures are facilitated where the two deformable rings 25 and 26 are coextensive in area and are each of uniform thickness, since such layers may be formed as a laminate, die cut to shape simultaneously, formed by pressure (or vacuum) and/or heat into the convex configuration shown in FIG. 1, and adhesively secured to the proximal face of rigid support ring 24.

As indicated by phantom lines 31 in FIGS. 1-3, the adhesive proximal face of the skin barrier ring 26 would be covered by a removable protective release film. That film, which may be formed of silicone-coated polyethylene or other suitable plastic material, is preferably of larger diameter than the pressure ring assembly (to protect the outer edge of the barrier ring 26) and may have tabs 31a to facilitate removal of the release film by a user. Similarly, the proximal surfaces of the skin barrier layer 16 of the faceplate, and the adhesive surface of the microporous patch 17, may also be covered by suitable release layers (not shown).

Figure 6:
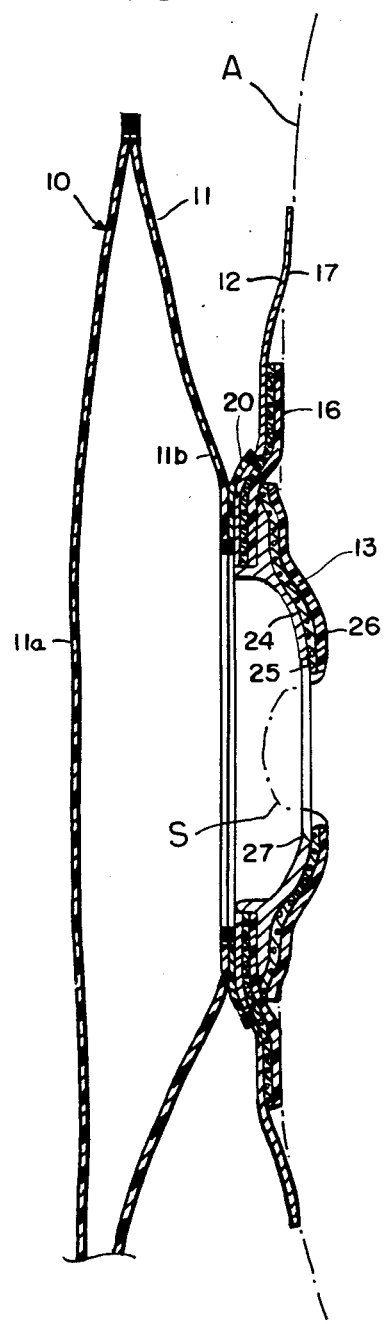
FIG. 6 is a vertical sectional view similar to FIG. 5 but illustrating the effect of the convex pressure ring assembly in causing protrusion of a flush or retracted stoma.

The pressure ring assembly 13 may be supplied to the user in the form illustrated in FIGS. 1-3, in which case the user would simply join the pressure ring assembly to the faceplate of an ostomy appliance in the manner depicted in FIGS. 4 and 5. Alternatively, such operations may be performed during manufacture so that the product as supplied to the user would take the assembled form depicted in FIG. 5. (In either case, as already described, barrier layer 16 and/or foam layer 18 may be omitted.) After removing the protective release films, the assembled appliance would simply be urged into place against the abdominal wall A of the patient. Because of its convex configuration, the ring assembly 13 presses inwardly against the abdomen in the immediate peristomal region, causing protrusion of the stoma S as somewhat schematically depicted in FIG. 6. It will be observed that the faceplate 12 tends to conform with the contour of the body but that the pressure ring assembly maintains it convex shape because of the rigidity of support ring 24. Since the openings through the barrier ring 26 and foam ring 25 are smaller than opening 27 in the support ring, the stoma is protected against direct contact with the rigid support ring.

Figure 7:
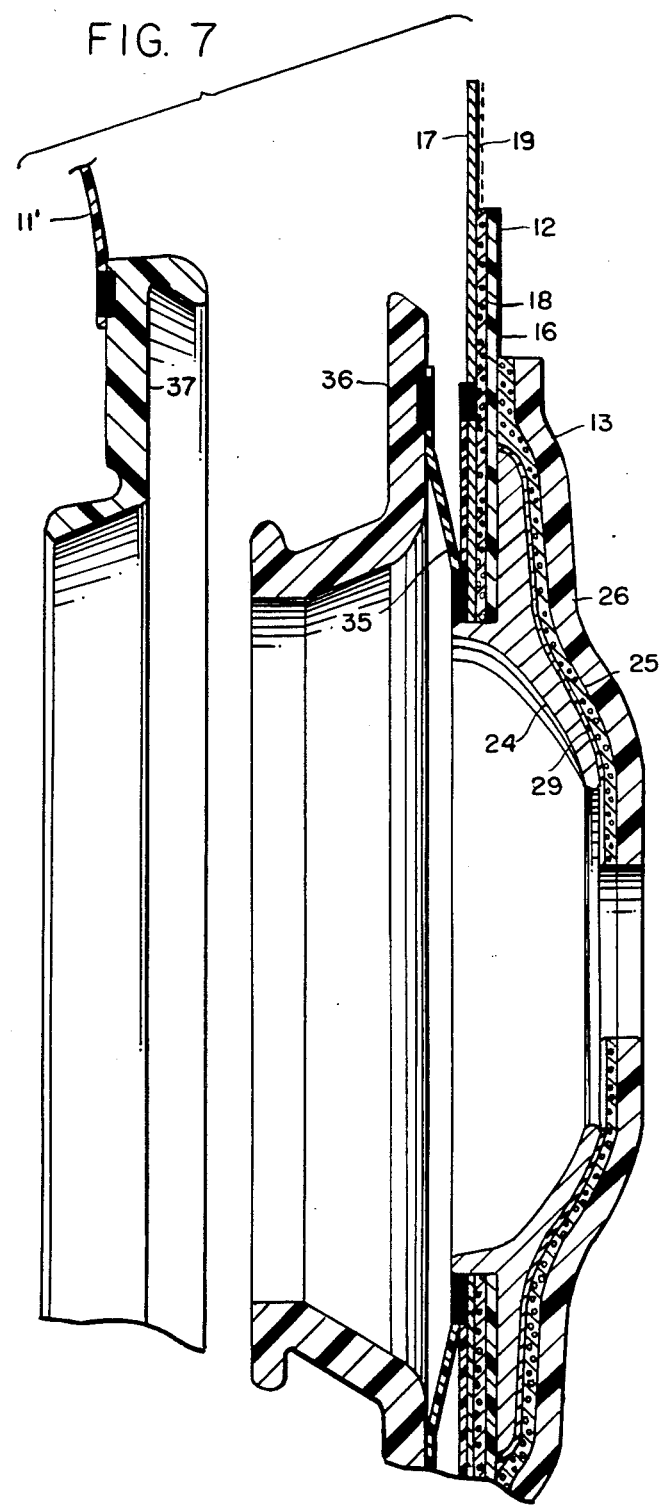
FIG. 7 is a fragmentary vertical sectional view of a second embodiment in which the convex pressure ring assembly of this invention is utilized in combination with what is commonly referred to as a two-piece appliance in which the adhesive faceplate and collection pouch are detachably connected by a pair of flexible coupling rings.

FIGS. 1-6 depict the pressure ring assembly 13 as part of what is commonly referred to as a one-piece ostomy appliance. The same pressure ring assembly may be used with a two-piece appliance as illustrated in FIG. 7. The pressure ring assembly and faceplate of FIG. 7 are the same in all essential respects as the parts illustrated in FIGS. 1-6; however, the faceplate, instead of being connected directly to a collection pouch, is joined by annular plastic web 35 to a faceplate coupling ring 36. Pouch 11' is equipped with its own pouch coupling ring 37. The flexible plastic coupling rings 36 and 37 are similar in structure and operation to those described in U.S. Pat. No. 4,610,678, the disclosure of which is incorporated by reference herein. The advantage of the construction shown in FIG. 7 is that a user wearing such a two-piece appliance may remove pouch 11' and replace it with a fresh pouch while leaving faceplate 12, convex pressure ring assembly 13, and coupling ring 36 attached to the body wall. While FIG. 7 illustrates one type of two-piece coupling, it is to be understood that other types of detachable coupling ring assemblies may be used to permit attachment and detachment of a faceplate and pouch.

It is significant that the pressure ring assembly in no way interferes with the operation of coupling rings 36 and 37. Unlike prior constructions in which convex inserts are required to be fitted in place from the distal side of a faceplate, assembly 13 is secured to the faceplate's proximal surface. Therefore, there is no danger that attachment of the convex pressure ring assembly might distort or damage the sealing surfaces of ring 36. Since the pressure ring assembly is not attached directly to coupling ring 36, and since assembly 13 is applied to the proximal surface of the faceplate, its configuration need not be compromised by the construction and operation of the coupling rings 36, 37.

The fact that the pressure ring assembly 13 is applied to the proximal side of a faceplate is also an important advantage when the pressure ring assembly is used with a one-piece appliance (FIGS. 1–6). Unlike prior convex inserts, assembly 13 is simply secured to the proximal surface of the faceplate, as shown in FIGS. 4 and 5, and is not secured to the inside of a pouch, on the distal side of a faceplate, after being inserted upwardly into the pouch through a lower drainage opening.

Figure 8:
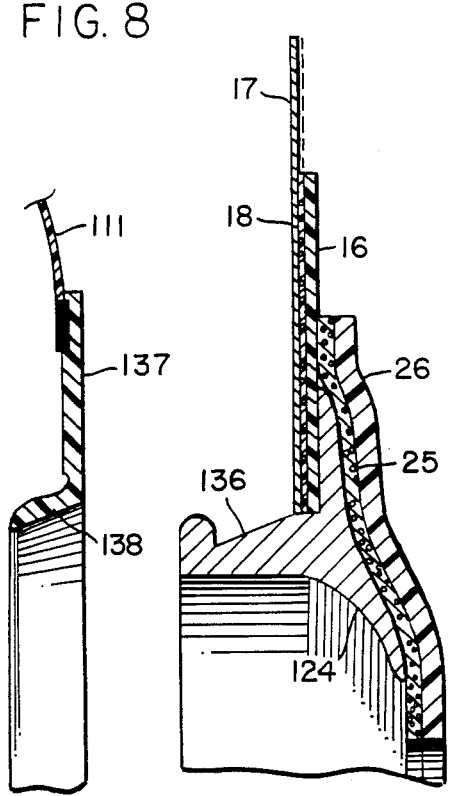
FIG. 8 is a fragmentary vertical sectional view of a third embodiment with the components of the two-piece appliance shown in separated condition.
Figure 9:
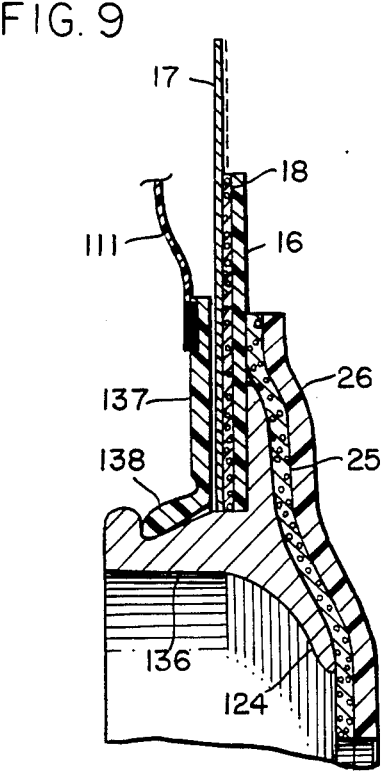
FIG. 9 is a sectional view showing the components of FIG. 8 in assembled condition.

FIGS. 8 and 9 also depict a two-piece appliance but, unlike the embodiment of FIG. 7, the faceplate coupling ring 136 is formed as an integral extension of rigid support ring 124. The annular extension 136 extends distally and the pouch coupling ring 137 includes an annular collar portion 138 that receives annular extension 136 when the parts are latched together as shown in FIG. 9. The result is a construction in which the support ring 124 performs dual functions of providing a convex pressure ring for causing stoma protrusion and providing the latching means for detachably coupling the faceplate to a pouch. Like the preceding embodiments, the construction of FIGS. 8 and 9 includes a barrier ring 26, an intermediate foam ring 25, and a microporous patch 17. If desired, a foam layer 18 and a skin barrier layer 16 may be interposed between the convex pressure ring assembly and the faceplate but, as previously indicated, such elements may be omitted.

Figure 10:
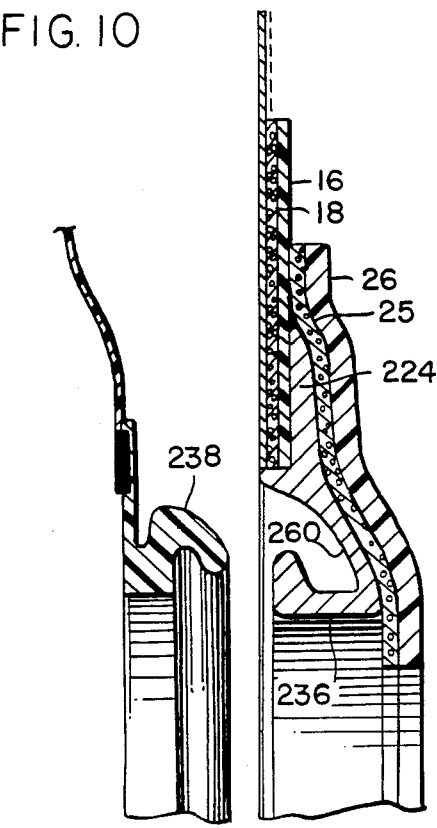
FIG. 10 is a fragmentary vertical sectional view of a fourth embodiment with the components of the two-piece appliance shown in separated condition.
Figure 11:
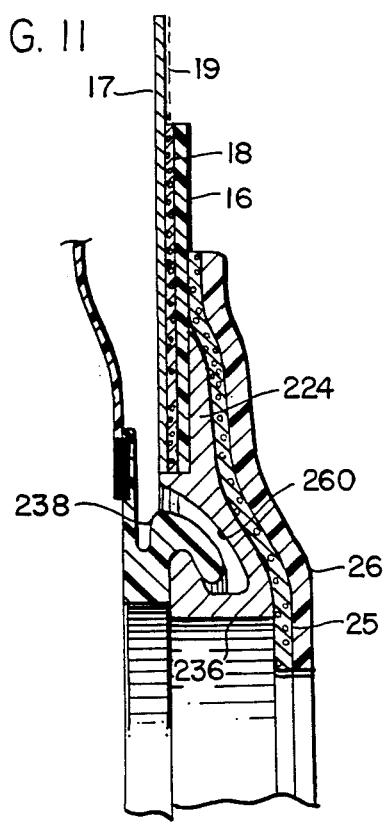
FIG. 11 is a sectional view showing the components of FIG. 10 in assembled condition.

FIGS. 10 and 11 illustrate how the profile of a two-piece appliance may be reduced by locating the latching elements 236 and 238 within the concavity 260 of rigid support ring 224. As in FIGS. 8 and 9, the latching or coupling ring 236 of the faceplate is an integral extension of rigid support ring 224; however, in contrast to the preceding embodiment, extension 236 is disposed within the distally-facing cavity of the support ring. When the coupling ring 237 of pouch 211 is brought into engagement with the coupling ring portion 236, the parts are nested together to provide an appliance which is of flat profile and in close proximity to a wearer's body. In other respects, the embodiment of FIGS. 10–11 is similar to those of the preceding embodiments.

While in the foregoing, embodiments of the invention have been disclosed in considerable detail for purposes of illustration, it will be understood by those skilled in the art that many of these details may be varied without departing from the spirit and scope of the invention.

We claim:

1. An ostomy appliance comprising a collection pouch formed of plastic film having a wall provided with a stoma opening; a flexible and generally planar faceplate having proximal and distal surfaces and having an opening therethrough aligned with said stoma opening of said pouch; adhesive means along said proximal surface for adhesively securing said faceplate to peristomal skin surfaces of a wearer; connecting means connecting said distal surface of said faceplate to said wall of said pouch about said stoma opening; wherein the improvement comprises a pressure ring assembly including a relatively rigid support ring having an annular wall with inner and outer wall portions; said inner wall portion having a central opening aligned with said openings of said faceplate and pouch and having a convex proximally-directed curvature; means securing the outer wall portion of said support ring to the proximal surface of said faceplate about said faceplate opening; an intermediate ring of resilient, moisture-impermeable, thermoformable material secured to and extending over the convex proximal surface of said support ring; and a barrier ring composed of soft, formable, moisture-absorbing skin barrier material of dry and wet tack secured to and covering the proximal surface of said intermediate ring.

2. The appliance of claim 1 in which said intermediate and barrier rings have openings therethrough aligned with and substantially smaller than said opening of said support ring.

3. The appliance of claims 1 or 2 in which each of said intermediate ring and said barrier ring is of substantially uniform thickness.

4. The appliance of claims 1 or 2 in which said intermediate ring is formed of soft, resilient, thermoplastic foam.

5. The appliance of claim 4 in which said foam ring is of thermoformed convex curvature conforming with the proximal surface contour of said support ring.

6. The appliance of claims 1 or 2 in which said faceplate comprises a layer of thin, microporous sheet material, and a layer of soft, deformable, moisture-absorbing skin barrier material having dry and wet tack extending over at least a portion of the proximal surface of said microporous layer.

7. The appliance of claims 1 or 2 in which said support ring includes an integral annular flange projecting distally into said opening of said faceplate.

8. An ostomy appliance comprising a collection pouch formed of plastic film having a wall provided with a stoma opening; a flexible and generally planar faceplate having proximal and distal surfaces and having an opening therethrough aligned with said stoma opening of said pouch; adhesive means along said proximal surface for adhesively securing said faceplate to peristomal skin surfaces of a wearer; connecting means connecting said distal surface of said wall of said pouch about said stoma opening; wherein the improvement comprises a pressure ring assembly including a relatively rigid support ring having an annular wall with inner and outer wall portions; said inner wall portion having a central opening aligned with said openings of said faceplate and pouch and having a convex proximally-directed curvature; means securing the outer wall portion of said support ring to the proximal surface of said faceplate about said faceplate opening; an intermediate ring of resilient, moisture-impermeable, thermoformable material secured to an extending over the convex proximal surface of said support ring; a barrier ring composed of soft, formable, moisture-absorbing skin barrier material of dry and wet tack secured to and covering the surface of said intermediate ring; said intermediate ring being formed of soft, resilient, thermoplastic foam, each of said foam and barrier rings having outer border portions extending radially outwardly beyond the periphery of said support ring; and means adhesively securing said border portions to said proximal surface of said faceplate.

9. The appliance of claim 8 in which said means for adhesively securing said border portions to said faceplate comprises a layer of skin barrier material of dry and wet tack extending over the proximal surface of said faceplate.

10. An ostomy appliance comprising a collection pouch formed of plastic film having a wall provided with a stoma opening; a flexible and generally planar faceplate having proximal and distal surfaces and having an opening therethrough aligned with said stoma opening of said pouch; adhesive means along said proximal surface for adhesively securing said faceplate to peristomal skin surfaces of a wearer; connecting means connecting said distal surface of said wall of said pouch about said stoma opening; wherein the improvement comprises
a pressure ring assembly including a relatively rigid support ring having an annular wall with inner and outer wall portions; said inner wall portion having a central opening aligned with said openings of said faceplate and pouch and having a convex proximally-directed curvature; means securing the outer wall portion of said support ring to the proximal surface of said faceplate about said faceplate opening; an intermediate ring of resilient, moisture-impermeable, thermoformable material secured to and extending over the convex proximal surface of said support ring; a barrier ring composed of soft, formable, moisture-absorbing skin barrier material of dry and wet tack secured to an covering the surface of said intermediate ring; said faceplate comprising a layer of thin, microporous sheet material, a layer of soft, deformable, moisture-absorbing skin barrier material having dry and wet tack extending over at least a portion of the proximal surface of said microporous layer; and a layer of soft, resilient, fluid-impermeable, plastic foam being interposed between and secured to both said layer of microporous sheet material and said skin-barrier layer.

11. An ostomy appliance comprising a collection pouch formed of plastic film having a wall provided with a stoma opening; a flexible and generally planar faceplate having proximal and distal surfaces and having an opening therethrough aligned with said stoma opening of said pouch; adhesive means along said proximal surface for adhesively securing said faceplate to peristomal skin surfaces of a wearer; connecting means connecting said distal surface of said wall of said pouch about said stoma opening; wherein the improvement comprises
a pressure ring assembly including a relatively rigid support ring having an annular wall with inner and outer wall portions; said inner wall portion having a central opening aligned with said openings of said faceplate and pouch and having a convex proximally-directed curvature; means securing the outer wall portion of said support ring to the proximal surface of said faceplate about said faceplate opening; an intermediate ring of resilient, moisture-impermeable, thermoformable material secured to and extending over the convex proximal surface of said support ring; and a barrier ring composed of soft, formable, moisture-absorbing skin barrier material of dry and wet tack secured to and covering the surface of said intermediate ring; said connecting means comprising a coupling ring assembly; said coupling ring assembly including a faceplate coupling ring secured to said faceplate and a pouch coupling ring attached to said pouch; each of said coupling rings having latching portions permitting selective detachment and attachment thereof.

12. The appliance of claim 11 in which said latching portion of said faceplate coupling ring is formed integrally with said support ring.

13. The appliance of claim 12 in which said support ring has a concave distally-facing surface defining a cavity; said latching portion of said faceplate coupling ring being located within said cavity.

14. The assembly of claims 8, 10, or 11 in which said intermediate and barrier rings have openings therethrough aligned with and substantially smaller than said opening of said support ring.

15. A pressure ring assembly for an ostomy appliance including a collection pouch having a stoma opening and equipped wit a flexible faceplate having an opening aligned with the stoma opening of said pouch; said faceplate having an adhesive proximal surface for peristomal attachment to a wearer; said pressure ring assembly including a relatively rigid support ring having an annular wall with inner and outer wall portions; said inner wall portion having a central opening alignable with the openings of a faceplate and pouch and having a convex curvature projecting in a proximal direction; said outer wall portion being adapted for attachment to the proximal surface of a faceplate about the opening thereof; an intermediate ring of soft, resilient, moisture-impermeable, thermoplastic material secured to and extending over the convex proximal surface of said support ring; and a barrier ring composed of soft, deformable, moisture-absorbing skin barrier material of dry and wet tack secured to covering the proximal surface of said intermediate ring.

16. The assembly of claim 15 in which said intermediate and barrier rings have openings therethrough aligned with and substantially smaller than said opening of said support ring.

17. The assembly of claim 15 in which said intermediate ring is formed of soft, thermoplastic foam.

18. The assembly of claim 17 in which said foam intermediate ring has a thermoformed cross-sectional curvature conforming with the convex proximal surface contour of said support ring.

19. The assembly of claim 17 in which each of said foam and barrier rings are of substantially uniform thickness.

20. The assembly of claim 15 in which each of said intermediate and barrier rings have outer border portions extending radially outwardly beyond the periphery of said support ring.

21. The assembly of claim 15 in which said support ring includes an integral annular flange projecting distally therefrom at the merger of said inner and outer wall portions.

22. The assembly of claims 15 or 16 in which said wall of said rigid support ring includes distally-projecting integral latching means for detachably coupling a collection pouch thereto.

23. A pressure ring assembly for an ostomy appliance including a collection pouch having a stoma opening and equipped with a flexible faceplate having an opening aligned with the stoma opening of said pouch; said faceplate having an adhesive proximal surface for peristomal attachment to a wearer; said pressure ring assembly including a relatively rigid support ring having an annular wall with inner and outer wall portions; and inner wall portion having a central opening alignable with the openings of a faceplate and pouch and having convex curvature projecting in a proximal direction; said outer wall portion being adapted for attachment to the proximal surface of a faceplate about the opening thereof; and intermediate ring of soft, resilient, moisture-impermeable, thermoplastic material secured to and extending over the convex proximal surface of said support ring; and a barrier ring composed of soft, deformable, moisture-absorbing skin barrier material of dry and wet tack secured to covering the proximal surface of said intermediate ring; said assembly also including a faceplate as an element of said assembly; means securing the outer wall portion of said support ring to a proximal surface of said faceplate; said faceplate having its distal surface connected to a faceplate coupling ring adapted for detachable connection to a mating coupling ring of a collection pouch.

24. A pressure ring assembly for an ostomy appliance including a collection pouch having a stoma opening and equipped with a flexible faceplate having an opening aligned with the stoma opening of said pouch; said faceplate having an adhesive proximal surface for peristomal attachment to a wearer; said pressure ring assembly including a relatively rigid support ring having an annular wall with inner and outer wall portions; said inner wall portion having a central pg,31 opening alignable with the openings of a faceplate and pouch and having convex curvature projecting in a proximal direction; said outer wall portion being adapted for attachment to the proximal surface of a faceplate about the opening thereof; an intermediate ring of soft, resilient, moisture-impermeable, thermoplastic material secured to an extending over the convex proximal surface of said support ring; and a barrier ring composed of soft, deformable, moisture-absorbing skin barrier material of dry and wet tack secured to covering the proximal surface of said intermediate ring; said wall of said rigid support ring including distally-projecting integral latching means for detachable coupling a collection pouch thereto; said support ring having a distally-facing concave surface defining a cavity; said latching means being located within said cavity.

25. The assembly of claims 23 or 24 in which said intermediate and barrier rings have openings therethrough aligned with an substantially smaller than said opening of said support ring.

* * * * *